US011859204B2

United States Patent
Yoon et al.

(10) Patent No.: US 11,859,204 B2
(45) Date of Patent: Jan. 2, 2024

(54) MOLD FOR PRODUCING HYDROGEL SUPPORT FOR THREE-DIMENSIONAL CELL CULTURE AND METHOD FOR PRODUCING HYDROGEL SUPPORT USING SAME

(71) Applicant: PUSAN NATIONAL UNIVERSITY INDUSTRY-UNIVERSITY COOPERATION FOUNDATION, Busan (KR)

(72) Inventors: Sik Yoon, Busan (KR); Ye Seon Lim, Yangsan-si (KR); Ye Jin Ok, Busan (KR); Sun Young Hwang, Busan (KR); Kang Oh Lee, Busan (KR); Seung Soo Lee, Busan (KR)

(73) Assignee: PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 674 days.

(21) Appl. No.: 16/962,851

(22) PCT Filed: Nov. 26, 2018

(86) PCT No.: PCT/KR2018/014642
§ 371 (c)(1),
(2) Date: Jul. 17, 2020

(87) PCT Pub. No.: WO2019/146896
PCT Pub. Date: Aug. 1, 2019

(65) Prior Publication Data
US 2020/0347349 A1 Nov. 5, 2020

(30) Foreign Application Priority Data
Jan. 25, 2018 (KR) .................. 10-2018-0009311

(51) Int. Cl.
*B29C 39/36* (2006.01)
*C12N 5/00* (2006.01)
*B29C 39/26* (2006.01)

(52) U.S. Cl.
CPC .......... *C12N 5/0062* (2013.01); *B29C 39/265* (2013.01); *B29C 39/36* (2013.01);
(Continued)

(58) Field of Classification Search
CPC ................ C12N 5/0062; C12N 5/0068; C12N 2513/00; C12N 2533/30; C12N 2535/00; B29C 39/265; B29C 39/36
See application file for complete search history.

(56) References Cited

U.S. PATENT DOCUMENTS 5,545,366 A    8/1996 Lust et al.
5,702,735 A *  12/1997 Martin ............. B29D 11/00028
                                              264/225

(Continued)

FOREIGN PATENT DOCUMENTS

EP    0765734 A2    4/1997
JP    11-034115 A   2/1999
(Continued)

OTHER PUBLICATIONS

Kalima et al ("Transparent thermoplastics: Replication of diffractive optical elements using micro-injection molding;" Optical Materials 30 (2007) 285-291) (Year: 2007).*

(Continued)

*Primary Examiner* — Anoop K Singh
*Assistant Examiner* — Suzanne E Ziska
(74) *Attorney, Agent, or Firm* — Revolution IP, PLLC

(57) ABSTRACT

A mold for producing a hydrogel support for a 3-dimensional (3D) cell culture, includes: an upper mold comprising a base and a plurality of upper unit molds protruding downward from the base to form accommodating portions of a female type corresponding to shapes of hydrogel supports, having through holes at bottoms thereof, and patterned at a lower portion of the base; a lower mold where a plurality of
(Continued)

lower unit molds are patterned, the plurality of lower unit molds formed in a female type to respectively accommodate the plurality of upper unit molds protruding downward and having sealed lower portions; and an ejecting unit for separating, from the accommodating portions of the plurality of upper unit molds, the hydrogel supports that are coagulated after being inserted into the through holes respectively formed in the plurality of upper unit molds.

9 Claims, 9 Drawing Sheets

(52) U.S. Cl.
CPC ........ *C12N 5/0068* (2013.01); *C12N 2513/00* (2013.01); *C12N 2533/30* (2013.01); *C12N 2535/00* (2013.01)

(56) References Cited

U.S. PATENT DOCUMENTS

| | | | |
|---|---|---|---|
| 5,709,827 A | * | 1/1998 | Andersen ................. B65D 5/00 264/102 |
| 2013/0188123 A1 | * | 7/2013 | Dean ...................... G02C 7/021 264/2.6 |

FOREIGN PATENT DOCUMENTS

| | | |
|---|---|---|
| KR | 10-2010-0091629 A | 8/2010 |
| KR | 10-2011-0039610 A | 4/2011 |
| KR | 10-1721514 B1 | 3/2017 |

OTHER PUBLICATIONS

International Search Report for PCT/KR2018/014642 dated Apr. 30, 2019 from Korean Intellectual Property Office.

* cited by examiner

MOLD FOR PRODUCING HYDROGEL SUPPORT FOR THREE-DIMENSIONAL CELL CULTURE AND METHOD FOR PRODUCING HYDROGEL SUPPORT USING SAME

TECHNICAL FIELD

The present disclosure relates to a mold for producing a hydrogel support for 3-dimensional (3D) cell culture and a method for producing a hydrogel support by using the same, and more particularly, to a mold for producing a support of a hydrogel material for culturing cells separated from a biological tissue, and a method for producing a hydrogel support by using the same.

BACKGROUND ART

Generally, the tissue engineering is in an academic field to be applied for clinical treatment purposes by maintaining, enhancing, and restoring or replacing biologic functions by using a combination of key elements of the engineering and life sciences, i.e., biological cells, engineering, materials, and appropriate biochemical/physiochemical factors. The most important technology in such tissue engineering may be attaching cells that are separated from a biological tissue and cultured to a porous support formed of a biodegradable polymer to be transplanted into a living body or generating a new biological tissue by culturing the cells in vitro for a certain period of time.

Meanwhile, culturing eukaryotic cells on a matrix formed of a simple 2-dimensional (2D) polystyrene or glass has a limitation that a physiological environment of a living body cannot be accurately reflected compared to allowing cells to grow in 3D by attaching eukaryotic cells to an extracellular matrix. Therefore, in order to implement many complex life phenomena (for example, expression of a receptor, transcription regulation of a gene, movement of a cell, and apoptosis) occurring in an actual biological tissue environment, a culture of 3D cells considering a spatial organization of cells has a very significant importance.

In relation to such a cell culture, an Internet public technology (http://imedifab.com/sub.asp?maincode=453&sub_sequence=465&sub_sub_sequence=477) discloses a method of producing a hydrogel support for 3D cell culture.

Here, such a conventional method of producing a hydrogel support is characterized in gelating a gel-phase material in a kit and then manually separating a gelated hydrogel support from the kit by using tweezers or the like.

As such, according to the conventional method of producing a hydrogel support, the gelated hydrogel support needs to be separated individually by using the tweezers, and thus a high skill level of an operator is required and work efficiency is low.

DESCRIPTION OF EMBODIMENTS

Technical Problem

The present disclosure has been made to solve the above problems and has an object of providing a mold for producing a hydrogel support for a 3-dimensional (3D) cell culture, which is improved such that a hydrogel support is easily separated and moved without a high skill level, and a method for producing a hydrogel support by using the same.

Solution To Problem

Aspects of one or more exemplary embodiments provide a mold for producing a hydrogel support for a 3-dimensional (3D) cell culture, the mold including: an upper mold including a base and a plurality of upper unit molds protruding downward from the base to form accommodating portions of a female type corresponding to shapes of hydrogel supports, having through holes at bottoms thereof, and patterned at a lower portion of the base; a lower mold where a plurality of lower unit molds are patterned, the plurality of lower unit molds formed in a female type to respectively accommodate the plurality of upper unit molds protruding downward and having sealed lower portions; and an ejecting unit for separating, from the accommodating portions of the plurality of upper unit molds, the hydrogel supports that are coagulated after being inserted into the through holes respectively formed in the plurality of upper unit molds.

The ejecting unit may include: a head portion having elasticity; and a stem portion connected to a lower portion of the head portion.

The head portion may be formed of silicon or rubber having elasticity.

An upper surface of the head portion contacting the hydrogel supports may be coated with styrene acrylonitrile copolymers (SAN) or polyethylene terephthalate glycol (PETG).

A cross section of the head portion may have a parabolic shape with an opened upper portion.

The cross section of the head portion may have a trumpet shape bending externally.

The ejecting unit may include: a connecting rod; a plurality of ejector pins combined to an upper portion of the connecting rod, patterned to correspond to the plurality of upper unit molds, and respectively inserted into the through holes formed in the plurality of upper unit molds; and a handle combined to a lower portion of the connecting rod and gripped by an operator.

Each of the plurality of ejector pins may include: a head portion having elasticity; and a stem portion connected to a lower portion of the head portion.

The mold may further include a packing unit mounted on an inner bottom surface of each of the plurality of lower unit molds to contact a lower portion of each of the plurality of upper unit molds and sealing each of the through holes.

The packing unit may be formed of a material selected from among ethylene propylene diene monomer rubber, polyurethane, fluorocarbon-based synthetic rubber, and hydrogenated nitrile butadiene rubber.

According to another aspect of the present disclosure, there is provided a method for producing a hydrogel support for a 3-dimensional (3D) cell culture, the method including: (A) preparing an upper mold including a base and a plurality of upper unit molds protruding downward from the base to form accommodating portions of a female type corresponding to shapes of hydrogel supports, having through holes at bottoms thereof, and patterned at a lower portion of the base; (B) preparing a lower mold where a plurality of lower unit molds are patterned, the plurality of lower unit molds formed in a female type to respectively accommodate the plurality of upper unit molds protruding downward and having sealed lower portions; (C) mounting the upper mold on the lower mold such that the plurality of upper unit molds are respectively inserted into the plurality of lower unit molds; (D) filling a gel-phase material in the accommodating portions of the upper mold; (E) coagulating the gel-phase material accommodated in the accommodating portions of the upper mold; (F) separating the upper mold from the lower mold; and (G) extracting completed hydrogel supports from the accommodating portions of the upper mold by inserting an ejecting unit into the through holes formed on the upper mold.

(G) may include: preparing the ejecting unit including a head portion formed of silicon or rubber having elasticity and a stem portion connected to a lower portion of the head portion; and inserting the head portion of the ejecting unit into the through holes formed on the upper mold from the bottom of the upper mold.

(G) may include: preparing the ejecting unit including a connecting rod, a plurality of ejector pins combined to an upper portion of the connecting rod and patterned to respectively correspond to the plurality of upper unit molds, and a handle combined to a lower portion of the connecting rod; and inserting the plurality of ejector pins of the ejecting unit into the through holes formed on the upper mold from the bottom of the upper mold.

The inserting of the plurality of ejector pins may include: locating the ejecting unit such that end portions of the plurality of ejector pins are respectively spaced apart from the plurality of upper unit molds by same intervals; and moving the ejecting unit towards the upper mold such that the end portions of the plurality of ejector pins are respectively and simultaneously inserted into the through holes of the plurality of upper unit molds.

(C) may include: preparing a packing unit formed of a material selected from among ethylene propylene diene monomer rubber, polyurethane, fluorocarbon-based synthetic rubber, and hydrogenated nitrile butadiene rubber; mounting the packing unit on an inner bottom surface of each of the plurality of lower unit molds; and mounting a lower portion of each of the plurality of upper unit molds on the packing unit such that each of the through holes are sealed by the packing unit.

Advantageous Effects of Disclosure

According to a mold for producing a hydrogel support for 3-dimensional (3D) cell culture and a method for producing a hydrogel support by using the same, according to the present disclosure, an upper mold is separated from a lower mold and then an ejecting unit is inserted into a through hole formed at a lower portion of the upper mold to separate a hydrogel support, and thus the hydrogel support can be easily separated and moved without a high skill level and work efficiency can be improved.

Also, according to a mold for producing a hydrogel support for 3D cell culture and a method for producing a hydrogel support by using the same, according to the present disclosure, a plurality of different hydrogel supports can be simultaneously produced by coagulating a gel-phase material in an accommodating portion of each of a plurality of upper unit mold.

MODE OF DISCLOSURE

Figure 1:
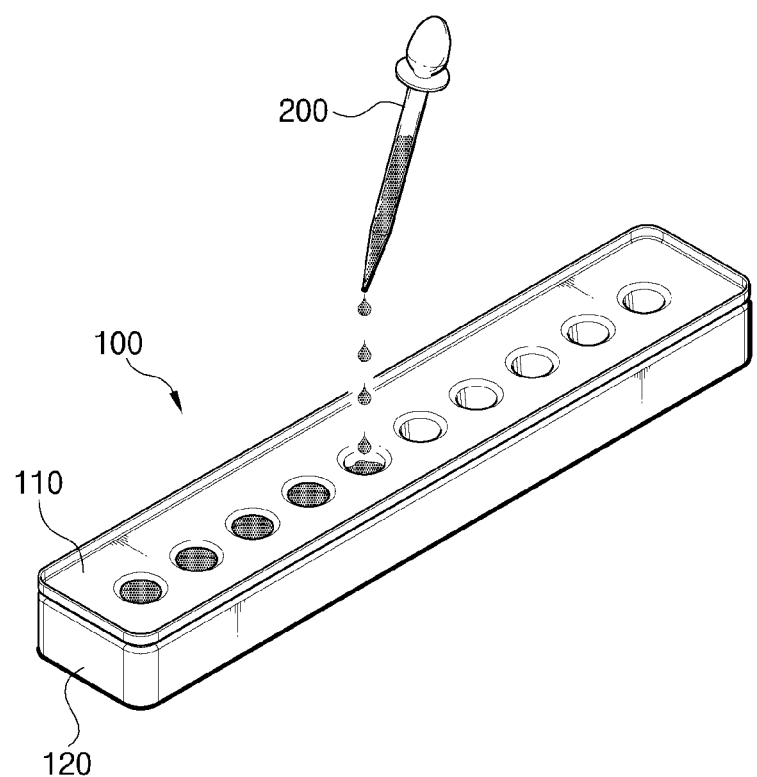
FIG. 1 is a perspective view showing a state in which an upper mold and a lower mold of a mold for producing a hydrogel support for a 3-dimensional (3D) cell culture are combined, according to an embodiment of the present disclosure.

Although the present disclosure has been described with reference to the embodiments shown in the drawings, these are merely exemplary, and one of ordinary skill in the art will understand that various modifications and other equivalent embodiments are possible therefrom. Therefore, the true technical protection scope of the present disclosure should be defined by the technical ideas of the appended claims.

Figure 2:
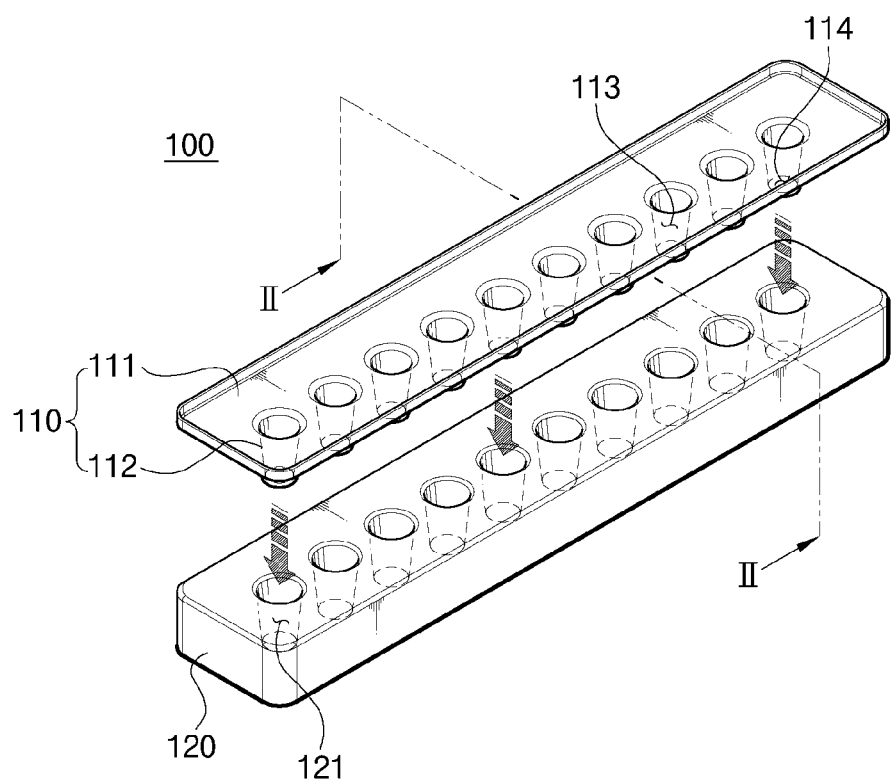
FIG. 2 is an exploded perspective view of the upper mold and the lower mold of FIG. 1.
Figure 3:
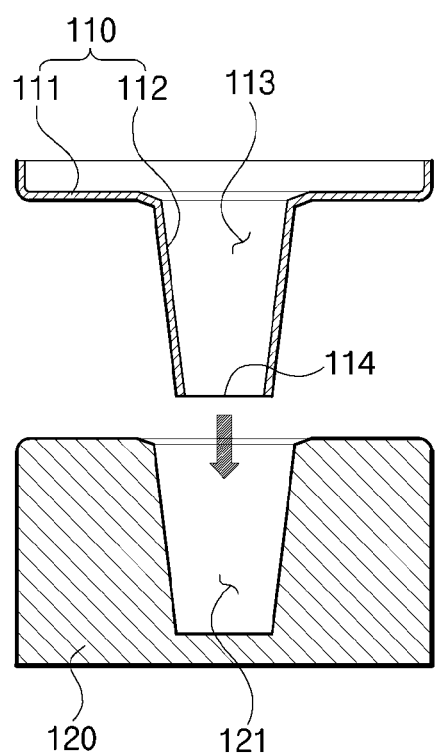
FIG. 3 is a cross-sectional view of the upper mold and the lower mold cut along a line II-II of FIG. 2.

FIG. 1 is a perspective view showing a state in which an upper mold and a lower mold of a mold for producing a hydrogel support for a 3-dimensional (3D) cell culture are combined, according to an embodiment of the present disclosure, FIG. 2 is an exploded perspective view of the upper mold and the lower mold of FIG. 1, and FIG. 3 is a cross-sectional view of the upper mold and the lower mold cut along a line II-II of FIG. 2.

Referring to the drawings, a mold 100 for producing a hydrogel support for a 3D cell culture, according to an embodiment of the disclosure (hereinafter, referred to as a 'mold'), includes an upper mold 110 and a lower mold 120.

The upper mold 110 includes a base 111 and a plurality of upper unit molds 112 provided at the base 111 and arranged to be spaced apart from each other at certain intervals. The base 111 is a member of a plate shape and is mounted on a top surface of the upper unit mold 112. The upper unit mold 112 protrudes downward from a lower surface of the base 111, has an accommodating portion 113 of a female type corresponding to a shape of the hydrogel support therein, and has a through hole 114 at a bottom thereof.

The lower mold 120 is arranged below the upper mold 110 and includes a plurality of lower unit molds 121 of a female type, which are arranged to be spaced apart from each other at certain intervals to correspond to the upper unit molds 112. Also, the upper mold 110 is mounted on a top portion of the lower mold 120 such that a bottom surface of the base 111 contacts a top surface of the lower mold 120 and the plurality of upper unit molds 112 are respectively inserted into the lower unit molds 121.

Here, an inner wall of the lower unit mold 121 may be formed to correspond to a shape of an outer wall of the upper unit mold 112. In other words, the upper mold 110 may be mounted on the lower mold 120 such that the outer wall of the upper unit mold 112 is completely adhered to the inner wall of the lower unit mold 121. In this case, as shown in FIG. 1, a gel-phase material filled in the accommodating portion 113 of the upper unit mold 112 via a pipette 200 may be prevented from leaking between the outer wall of the upper unit mold 112 and the inner wall of the lower unit mold 121.

Figure 4:
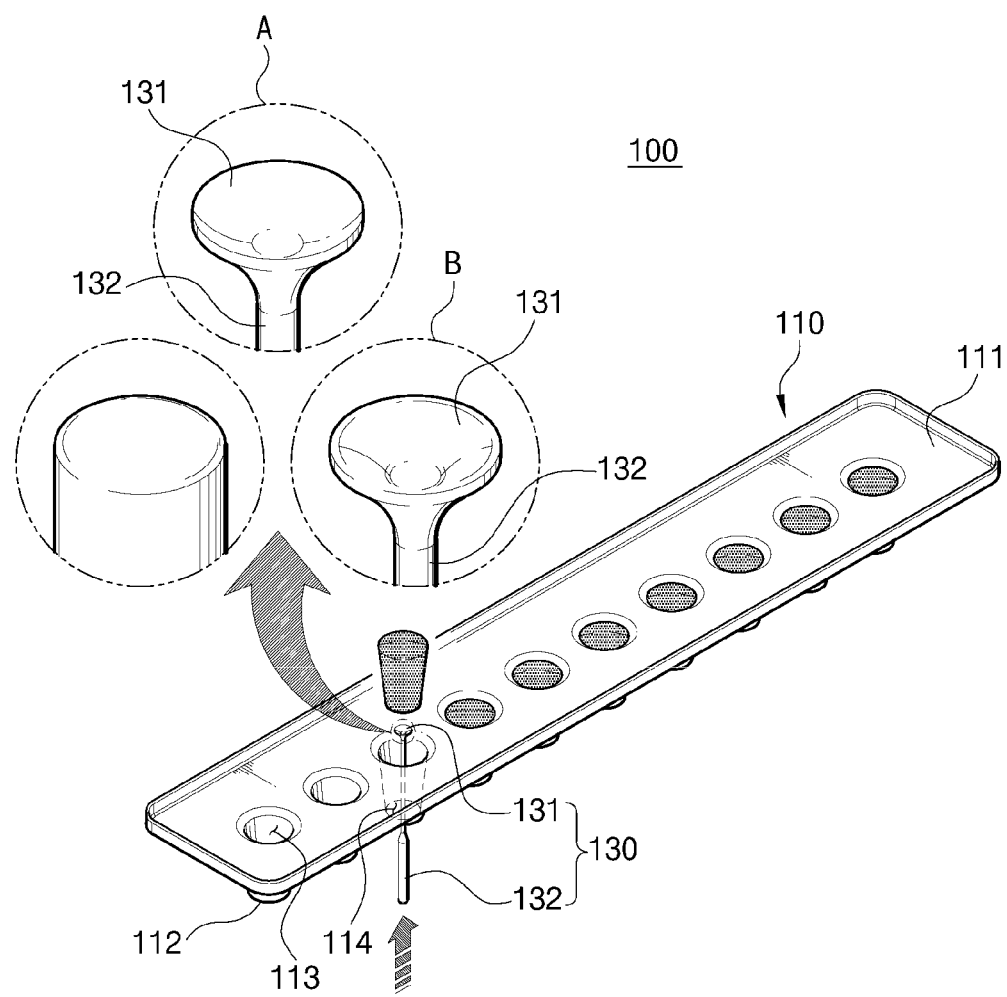
FIG. 4 is a perspective view showing an upper mold and a first ejecting unit of a mold for producing a hydrogel support, according to an embodiment of the present disclosure.
Figure 5:
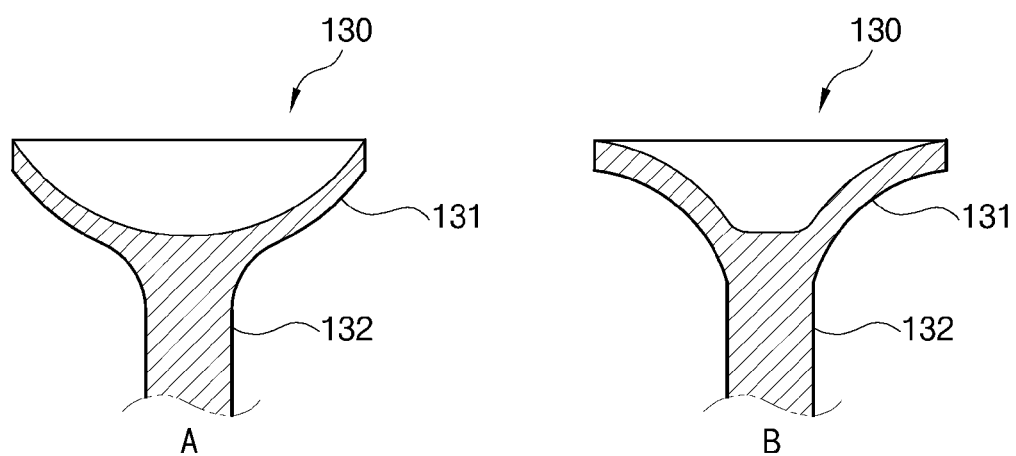
FIG. 5 is a longitudinal cross-sectional view of a head portion of the first ejecting unit of FIG. 4.
Figure 6:
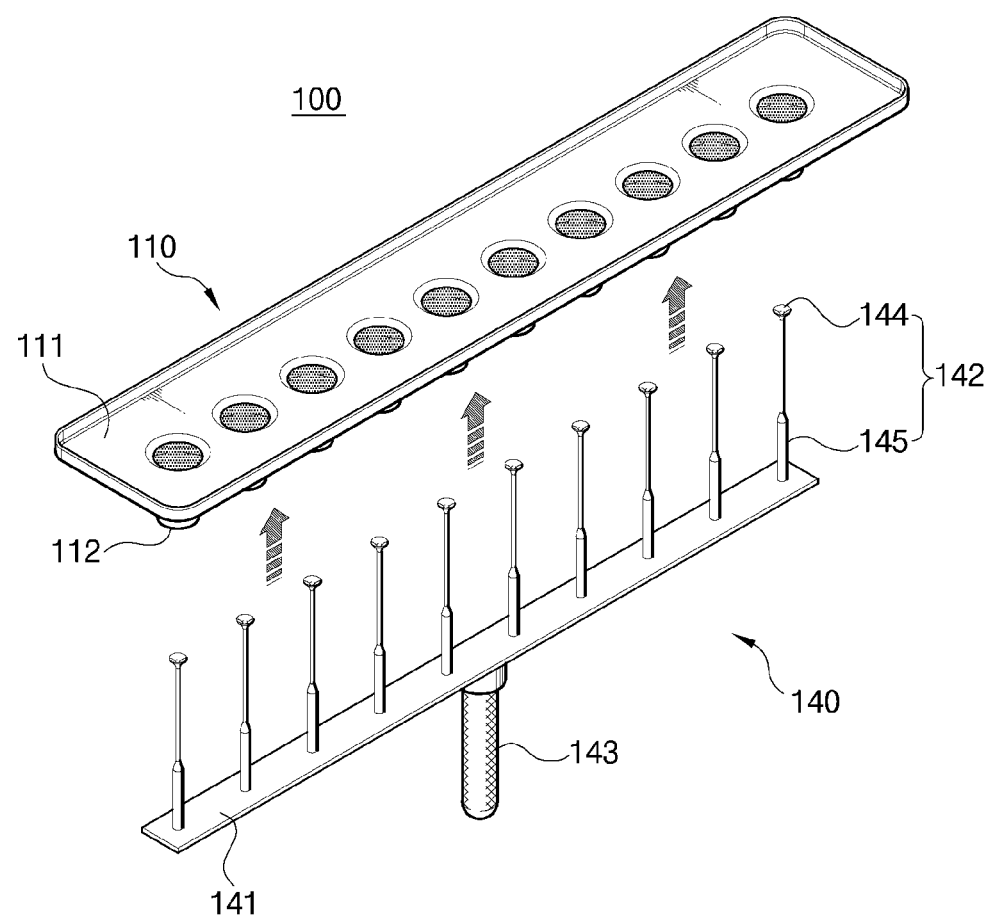
FIG. 6 is a perspective view showing an upper mold and a second ejecting unit of a mold for producing a hydrogel support, according to an embodiment of the present disclosure.

FIG. 4 is a perspective view showing an upper mold and a first ejecting unit of a mold for producing a hydrogel support, according to an embodiment of the present disclosure, FIG. 5 is a longitudinal cross-sectional view of a head portion of the first ejecting unit of FIG. 4, and FIG. 6 is a perspective view showing an upper mold and a second ejecting unit of a mold for producing a hydrogel support, according to an embodiment of the present disclosure.

Referring to the drawings, a mold 100 further includes an ejecting unit 130 or 140. The upper mold 110 is separated from the lower mold 120 after a hydrogel support is coagulated in the accommodating portion 113 of the upper mold 110. Then, the ejecting unit 130 or 140 are inserted into the through hole 114 of the upper mold 110 from the bottom of the separated upper mold 110 to separate the hydrogel support accommodated in the accommodating portion 113 of the upper mold 110 from the upper mold 110.

Here, the ejecting unit 130 or 140 may be classified as a first ejecting unit 130 or a second ejecting unit 140. As shown in FIG. 4, the first ejecting unit 130 may include a head portion 131 having elasticity and a stem portion 132 connected to a lower portion of the head portion 131. An operator may separate the hydrogel support from the upper mold 110 by gripping the stem portion 132 and inserting the head portion 131 into the through hole 114 of the upper mold 110.

Meanwhile, the coagulated hydrogel support is vulnerable to an external impact due to characteristics of its material. Thus, if the head portion 131 is formed of a solid material such as a metal, the hydrogel support may be damaged when the head portion 131 pushes the hydrogel support accommodated in the accommodating portion 113 of the upper mold 110. Thus, in order to prevent the damage, the head portion 131 may be formed of a material having elasticity, such as silicon or rubber. In this case, it is possible to prevent the head portion 131 from damaging the hydrogel support according to the elasticity of the head portion 131. However, this is only an embodiment of the present disclosure and the head portion 131 may be formed of an elastic material other than silicon and rubber.

An upper surface of the head portion 131, which contacts the hydrogel support, may be coated with styrene acrylonitrile copolymers (SAN) or polyethylene terephthalate glycol (PETG). SAN and PETG have excellent transparency and chemical resistance to thermal deformation and are widely used as antistatic agents, blocking agents, and the like. As such, when the head portion 131 is coated with SAN or PETG, a problem in which the head portion 131 is adhered to the hydrogel support and not separated may be resolved. However, this is only an embodiment of the present disclosure and the head portion 131 may be coated with a material other than SAN or PETG.

A cross section of the head portion 131 may have a parabolic shape with an opened upper portion. Here, the cross section of the head portion 131 may be formed in a parabolic shape bending inward from top to bottom as shown in a region A of FIG. 5 or in a trumpet shape bending outward from bottom to top as shown in a region B of FIG. 5. In this case, an outer circumference portion of the head portion 131 may be externally folded while being inserted into the through hole 114 of the upper mold 110 such that the head portion 131 is more smoothly inserted into the through hole 114.

As shown in FIG. 6, the second ejecting unit 140 may include a connecting rod 141, a plurality of ejector pins 142, and a handle 143. The connecting rod 141 is a member of a plate shape, and the plurality of ejector pins 142 and the handle 143 are installed thereto. The plurality of ejector pins 142 are arranged to be spaced apart from each other at certain intervals and combined to a top portion of the connecting rod 141 to correspond to the plurality of lower unit molds 121. The handle is combined to a bottom portion of the connecting rod 141. The operator may hold the handle 143 and push the connecting rod 141 towards the upper mold 110 to insert the plurality of ejector pins 142 respectively into the through holes 114 of the plurality of upper unit molds 112, thereby separating the hydrogel support from the upper mold 110.

Here, the operator may push the second ejecting unit 140 towards the upper mold 110 such that end portions of the plurality of ejector pins 142 are simultaneously and respectively inserted into the through holes 114 of the plurality of upper unit molds 112 while gripping the handle 143 such that the end portions of the plurality of ejector pins 142 are respectively spaced apart from the plurality of upper unit molds 112 at same intervals. In this case, a plurality of different hydrogel supports respectively accommodated in the accommodating portions 113 of the plurality of upper unit molds 112 may be easily separated from the upper mold 110 without any difficulty.

The ejector pin 142 may include a head portion 144 having elasticity and a stem portion 145 connected to a bottom portion of the head portion 144. The head portion 144 is inserted into the through hole 114 of the upper mold 110 to separate the hydrogel support accommodated in the accommodating portion 113 of the upper mold 110 from the upper mold 110. Also, the stem portion 145 is perpendicularly combined to a top portion of the connecting rod 141 to fix the head portion 144 to the connecting rod 141.

Meanwhile, it would be obvious that the head portion 144 of the second ejecting unit 140 may be formed of silicon or rubber like the head portion 131 of the first ejecting unit 130, and an upper surface thereof contacting the hydrogel support may be coated with SAN or PETG, and a cross section thereof may be formed in a parabolic shape with an opened top portion. Because this has been described in detail above, detailed descriptions thereof will be omitted.

Figure 9:
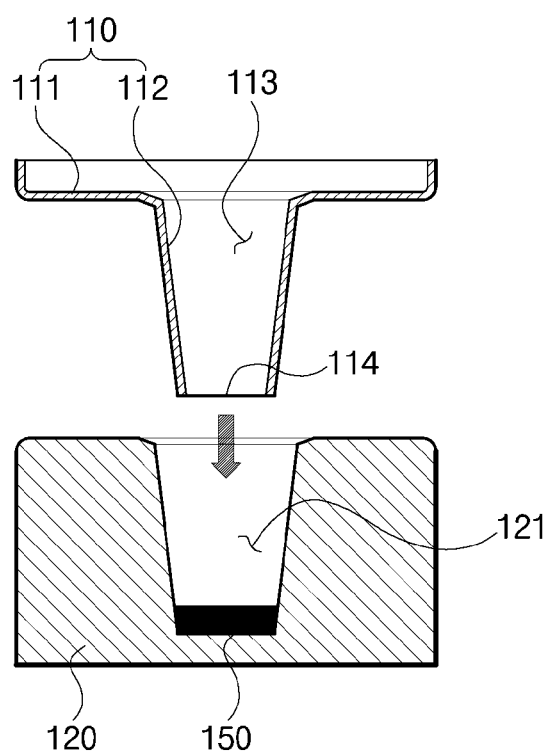
FIG. 9 is a view showing a state in which a packing unit is provided in FIG. 3.

Referring to FIG. 9, the mold 100 for producing a hydrogel support, according to the present disclosure, may further include a packing unit 150. The packing unit 150 is provided at an inner bottom surface of the lower unit mold 121. Also, a bottom portion of the upper unit mold 112 is mounted on a top portion of the packing unit 150. Accordingly, the packing unit 150 seals the through hole 114, thereby preventing the hydrogel support injected and coagulated inside the upper unit mold 112 from leaking between inner surfaces of the upper unit mold 112 and the lower unit mold 121.

The packing unit 150 may be formed of a material selected from among ethylene propylene diene monomer rubber, polyurethane, fluorocarbon-based synthetic rubber, and hydrogenated nitrile butadiene rubber.

Ethylene propylene diene monomer rubber is an amorphous polymer material obtained by co-polymerizing ethylene and propylene, and exhibits chemically stable characteristics. Polyurethane is a polymer compound formed via a combination of an alcohol group and an isocyanic acid group, and has excellent abrasion resistance, chemical resistance, and solvent resistance and has excellent aging resistance, i.e., stability to oxygen. Fluorocarbon-based synthetic rubber is a polymer compound containing fluorine in a molecule and has excellent chemical resistance, thermal resistance, and lubricity. Hydrogenated nitrile butadiene rubber is a polymer compound that is saturated with hydrogen in a butadiene segment to form a double bond, and has excellent thermal resistance, ozone resistance, and chemical resistance compared to existing nitrile butadiene rubber.

When the packing unit 150 formed of such a material is used, the hydrogel support may be prevented from being adhered to a top portion of the packing unit 150 while the hydrogel support is coagulated inside the upper unit mold 112.

Hereinafter, a method of producing a hydrogel support for a 3D cell culture by using the mold 100 will be described in detail.

Figure 7:
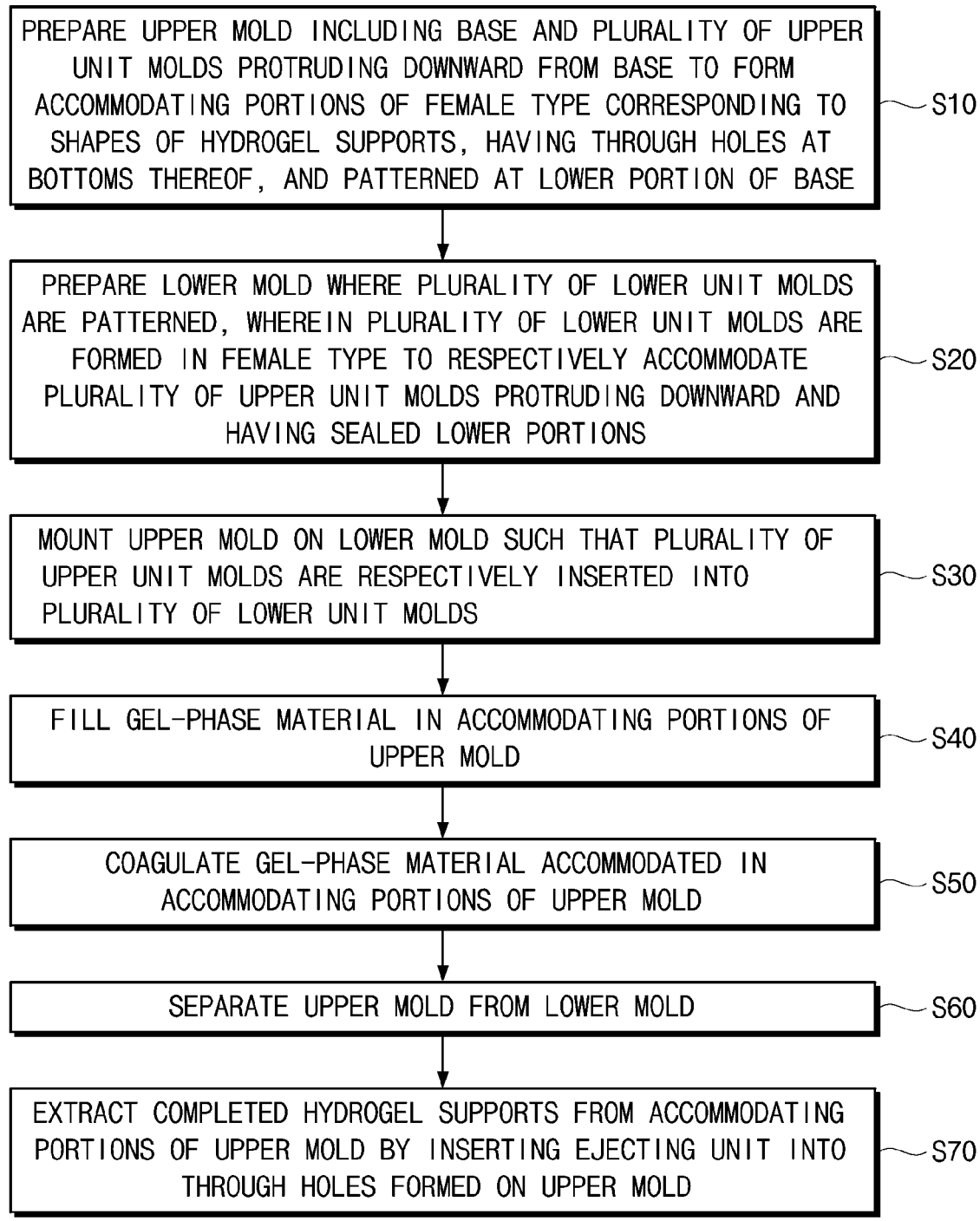
FIG. 7 is a flowchart of a method for producing a hydrogel support for a 3D cell culture, according to an embodiment of the present disclosure.
Figure 8:
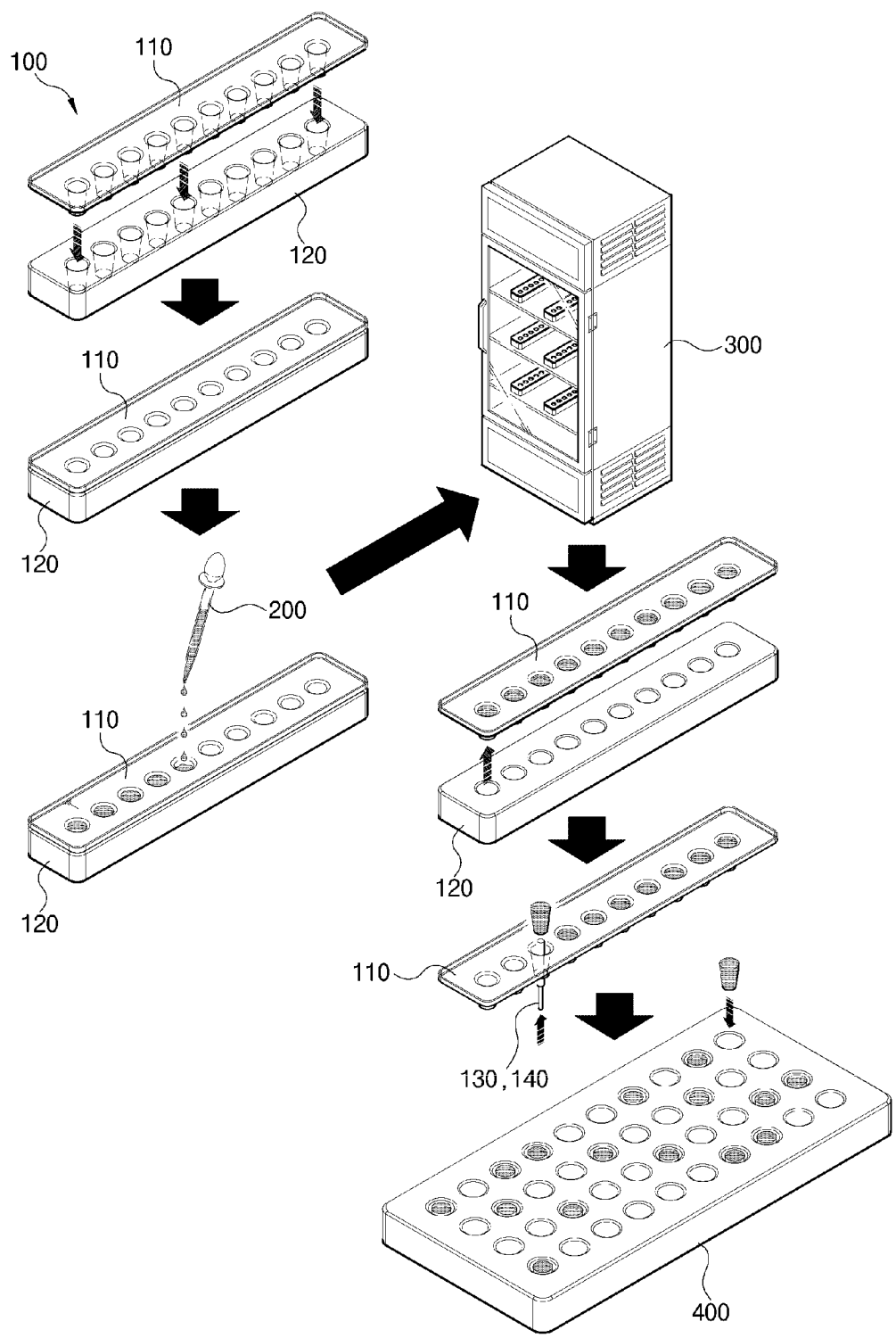
FIG. 8 is a perspective view showing processes in which a hydrogel support is produced according to the method of FIG. 7 for producing a hydrogel support for 3D cell culture.

FIG. 7 is a flowchart of a method for producing a hydrogel support for a 3D cell culture, according to an embodiment of the present disclosure, and FIG. 8 is a perspective view showing processes in which a hydrogel support is produced according to the method of FIG. 7 for producing a hydrogel support for 3D cell culture.

Referring to the drawings, in order to produce a hydrogel support for a 3D cell culture, according to an embodiment of the present disclosure, first, the upper mold 110 including the base 111 and the plurality of upper unit molds 112 protruding downward from the base 111 to form the accommodating portions 113 of a female type corresponding to shapes of the hydrogel supports, having the through holes 114 at the bottoms thereof, and patterned at the lower portion of the base 111 is prepared (operation S10). Then, the lower mold 120 where the plurality of lower unit molds 121 are patterned is prepared below the upper mold 110 (operation S20), wherein the plurality of lower unit molds 121 are formed in a female type to respectively accommodate the plurality of upper unit molds 112 protruding downward and have sealed lower portions. Next, the upper mold 110 is mounted on the top surface of the lower mold 120 such that the plurality of upper unit molds 112 are respectively inserted into the lower unit molds 121 (operation S30).

Here, in operation S30, the packing unit 150 may be provided between the upper unit mold 112 and the lower unit mold 121. In particular, in operation S30, the packing unit 150 formed of a material selected from among ethylene propylene diene monomer rubber, polyurethane, fluorocarbon-based synthetic rubber, and hydrogenated nitrile butadiene rubber is prepared. Then, the packing unit 150 is amounted on an inner bottom surface of the lower unit mold 121. Next, a bottom portion of the upper unit mold 112 is mounted on the packing unit 150 such that the through hole 114 is sealed by the packing unit 150. Through such a process, the upper mold 110 is mounted on the top surface of the lower mold 120 in operation S30.

Next, a gel-phase material is filled in each of the accommodating portions 113 of the upper mold 110 by using the pipette 200 (operation S40). Here, the operator may fill the same gel-phase material in each of the accommodating portions 113 of the plurality of upper unit molds 112 or fill different gel-phase materials in each of the accommodating portions 113 of the plurality of upper unit molds 112, according to a purpose of an operation.

Then, the upper mold 110 and the lower mold 120 are loaded into a coagulating apparatus 300 to coagulate the gel-phase materials accommodated in the accommodating portions 113 of the upper mold 110 (operation S50). After coagulating the gel-phase materials for a sufficient period of time, the upper mold 110 and the lower mold 120 are taken out from the coagulating apparatus 300 to separate the upper mold 110 from the lower mold 120 (operation S60).

Next, the ejecting unit 130 or 140 is located at the bottom portion of the separated upper mold 110. Then, an end portion of the ejecting unit 130 or 140 (the head portion 131 when the ejecting unit is the first ejecting unit 130 and the head portion 144 of the ejector pin 142 when the ejecting unit is the second ejecting unit 140) is inserted into the through holes 114 of the upper mold 110 to extract the hydrogel supports accommodated in the accommodating portions 113 of the upper mold 110 from the upper mold 110 (operation S70), thereby completing all producing processes of a hydrogel support for a 3D cell culture. Thereafter, the extracted hydrogel supports are moved to a cell culture plat 400 to perform a culturing process of a 3D cell, in which a cell separated from a human body is cultured on the hydrogel support.

Here, when the ejecting unit is the second ejecting unit 140, the operator may push the second ejecting unit 140 towards the upper mold 110 such that the end portions of the plurality of ejector pins 142 are respectively and simultaneously inserted into the through holes 114 of the plurality of upper unit molds 112 while gripping the handle 143 such that the end portions of the plurality of ejector pins 142 are respectively spaced apart from the plurality of upper unit molds 112 at same intervals. In this case, the plurality of different hydrogel supports respectively accommodated in the accommodating portions 113 of the plurality of upper unit molds 112 may be easily separated from the upper mold 110 without any difficulty.

As described above, according to the mold 100 for producing a hydrogel support for a 3D cell culture and the method of producing a hydrogel support by using the same, according to the present disclosure, a hydrogel support may be easily separated and moved without a high skill level and work efficiency may be improved by separating the upper mold 110 from the lower mold 120 and then inserting the ejecting unit 130 or 140 into the through hole 114 formed at a bottom portion of the upper mold 110 to separate a hydrogel support. Also, according to the mold 100 for producing a hydrogel support for a 3D cell culture and the method of producing a hydrogel support by using the same, according to the present disclosure, a plurality of different hydrogel supports may be simultaneously produced by coagulating gel-phase materials respectively in accommodating portions of the plurality of upper unit molds 112.

The invention claimed is:

1. A mold for producing a hydrogel support for a 3-dimensional (3D) cell culture, the mold comprising:
    an upper mold comprising a base and a plurality of upper unit molds protruding downward from the base to form accommodating portions of a female type corresponding to shapes of hydrogel supports, having through holes at bottoms thereof, and patterned at a lower portion of the base;
    a lower mold where a plurality of lower unit molds are patterned, the plurality of lower unit molds formed in a female type to respectively accommodate the plurality of upper unit molds protruding downward and having sealed lower portions; and
    an ejecting unit for separating, from the accommodating portions of the plurality of upper unit molds, the hydrogel supports that are coagulated after being inserted into the through holes respectively formed in the plurality of upper unit molds, wherein the ejecting unit comprises:
    a head portion having elasticity; and
    a stem portion connected to a lower portion of the head portion,
wherein the head portion is formed to have a larger area than the stem portion,
wherein an area of the head portion gradually increases from one end to the other end of the head portion,
wherein each of the through holes of the upper mold has a size corresponding to the other end of the head portion so that the other end of the head portion is configured to pass through each through hole.

2. The mold of claim 1, wherein the head portion is formed of silicon or rubber having elasticity.

3. The mold of claim 1, wherein an upper surface of the head portion contacting the hydrogel supports are coated with styrene acrylonitrile copolymers (SAN) or polyethylene terephthalate glycol (PETG).

4. The mold of claim 1, wherein a cross section of the head portion has a parabolic shape with an opened upper portion.

5. The mold of claim 4, wherein the cross section of the head portion has a trumpet shape bending externally.

6. The mold of claim 1, wherein the ejecting unit comprises:
    a connecting rod;
    a plurality of ejector pins combined to an upper portion of the connecting rod, patterned to correspond to the plurality of upper unit molds, and respectively inserted into the through holes formed in the plurality of upper unit molds; and
    a handle combined to a lower portion of the connecting rod and gripped by an operator.

7. The mold of claim 6, wherein each of the plurality of ejector pins comprises:
    a head portion having elasticity; and
    a stem portion connected to a lower portion of the head portion.

8. The mold of claim 1, further comprising a packing unit mounted on an inner bottom surface of each of the plurality of lower unit molds to contact a lower portion of each of the plurality of upper unit molds and sealing each of the through holes.

9. The mold of claim 8, wherein the packing unit is formed of a material selected from among ethylene propylene diene monomer rubber, polyurethane, fluorocarbon-based synthetic rubber, and hydrogenated nitrile butadiene rubber.

* * * * *